DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED NOVEMBER 7, 1972

904 O.G. 8

T904,011

PROCESS FOR REMOVING METHYL p-FORMYLBENZOATE FROM MIXTURES AND NOVEL ANILS OBTAINED THEREFROM

Edward U. Elam, 702 Yadkin St. 37662, and Max A. Weaver, Rte. 8 37664, both of Kingsport, Tenn.

Filed Jan. 28, 1972, Ser. No. 221,760
Int. Cl. C07c *101/42*
U.S. Cl. 260—471 R
No Drawing. 9 Pages Specification

Process for removing methyl p-formylbenzoate from a mixture thereof with one or more other esters of aryl carboxylic or dicarboxylic acids by adding to a solution of the mixture a primary arylamine to form an insoluble anil of the arylamine and methyl p-formylbenzoate and recovering the anil.